United States Patent [19]

Hinkley et al.

[11] Patent Number: 5,694,807
[45] Date of Patent: Dec. 9, 1997

[54] APPARATUS AND METHOD FOR DETERMINING THE MASS DENSITY OF A FILAMENT

[75] Inventors: Jeffrey A. Hinkley, Yorktown; Joseph M. Marchello, Hampton, both of Va.

[73] Assignee: The United States of America as represented by the Administrator of the National Aeronautics and Space Administration, Washington, D.C.

[21] Appl. No.: 316,708

[22] Filed: Sep. 29, 1994

[51] Int. Cl.⁶ ........................................... G01L 5/04
[52] U.S. Cl. ........................................ 73/160; 73/159
[58] Field of Search ........................... 73/159, 160

[56] References Cited

U.S. PATENT DOCUMENTS

| | | | |
|---|---|---|---|
| 3,945,181 | 3/1976 | Yamazaki et al. | 73/160 X |
| 4,580,132 | 4/1986 | Kato et al. | 73/160 X |
| 4,610,707 | 9/1986 | Grundy | 73/159 X |
| 4,764,876 | 8/1988 | Whitener et al. | 73/160 X |
| 4,953,400 | 9/1990 | Bossuyt | 73/159 |
| 5,146,550 | 9/1992 | Furter et al. | 73/160 X |
| 5,270,787 | 12/1993 | Shofner et al. | 73/160 X |

*Primary Examiner*—Elizabeth L. Dougherty
*Attorney, Agent, or Firm*—George F. Helfrich

[57] ABSTRACT

A method and apparatus for determining the mass density of a moving filament is provided. The method includes the steps of providing a filament across two supports, tensioning the filament, inducing a vibration into the filament segment between the supports, reinforcing the vibration using an amplified feedback signal, detecting the vibrational frequency data, processing the data using a fast-fourier transform analysis, and then displaying the frequency. The use of the feedback signal results in a self-tuning resonant loop. Open loop versions may also be used. The apparatus includes a base supporting a fixed support and a transducer which in turn supports a moveable support. The transducer vibrates the moveable support transversely to the direction of travel of the filament, thereby inducing a transverse vibrational mode. The output of the transducer is amplified and used to drive a second amplifier to produce a self-tuning resonant loop. In the open loop version a signal generator is used to drive the transducer through a frequency range, during which the amplitude peak is identified.

12 Claims, 7 Drawing Sheets

APPARATUS AND METHOD FOR DETERMINING THE MASS DENSITY OF A FILAMENT

ORIGIN OF THE INVENTION

The invention described herein was jointly made in the performance of work under NASA Grant No. NAG-1-1067 and an employee of the United States Government. In accordance with 35 USC 202, the Grantee elected not to retain title.

BACKGROUND OF THE INVENTION

The invention relates to testing and measurement, and more particularly to mass measurement of filaments using vibrational dynamics.

In the preparation of impregnated yarns or fiber tows to be used, for example, in the manufacture of fiber reinforced composites, it is necessary to know the amount of resin being applied. The prior method for determining the resin content was to cut a known length of the yarn and weigh it. Obviously, this method required interrupting the production process. Other known methods, such as capacitance and radiation measurements, for determining resin content for quality control also have drawbacks. Capacitance gauges require close tolerances (difficult to achieve with non-uniform yarn) and are sensitive to EM interference, necessitating extensive filtering and long settling times. Various radiation gauges (beta, gamma) may work, but are expensive and contain potentially hazardous radioisotopes. More recent prior art has been directed toward evaluating mechanical properties by determining vibrational response of a section of fiber. U.S. Pat. No. 5,269,181, Dec. 14, 1993 by Gibson et al provide for testing of a fiber by inducing a longitudinal pulse into section of fiber to which a weight has been attached.

The object of the Gibson device is to evaluate longitudinal oscillatory response in order to determine mechanical properties such as dynamic modulus and damping. Fiber reinforced materials are increasingly used in automotive and aerospace applications. During production of the reinforcing fibers, resin is added to the fiber during production line operations. Typically, a continuous filament moving a high speed is brought in contact with the resin applicator and thereafter continues to a fabricating device where the fiber is wound around a nose cone or structure. In order to maintain optimized strength-to-weight and stiffness-to-weight ratios accurate control of the resin content must be established. It is preferable to control resin content without stopping the production line and without removing the fiber from the line process.

SUMMARY OF THE INVENTION

Accordingly, it is an object of the present invention to provide an apparatus and method for measuring mass density of a filament, yarn, tape, wire or like material.

It is another object of the invention to provide a means of measuring mass density on a continuous filament.

It is yet another object of the invention to provide a means of measuring mass density of a moving filament.

The method of the invention comprises the steps of: providing two supports for a filament to be tested; leading a filament across the supports; tensioning the filament; inducing a transverse vibration into the filament; detecting the frequency of vibration; amplifying the frequency; feeding the amplified signal back to further excite filament vibration; and displaying the vibrational signal. The apparatus comprises a base having a fixed filament support attached thereto and having a transducer attached thereto. A moveable filament support is attached to the free side of the transducer and this support is vibrated in a plane transverse to the path of the filament thereby inducing transverse vibrations in the filament. A light source and a photodetector are mounted on the base on either side of the path of the moving filament. An optical mask is mounted between the light source and the photodetector to allow detecting of the filament vibrational movement. The signal generated by the photodetector is amplified and used to provide feedback to the transducer thereby producing an augmented resonance response from the filament. This signal is then displayed to give a measure of filament density.

BRIEF DESCRIPTION OF THE DRAWINGS

For a more complete understanding of the present invention and for further objects and advantages thereof, reference is now made to the following description taken in conjunction with the accompanying drawings in which.

DETAILED DESCRIPTION OF THE INVENTION

Figure 1:
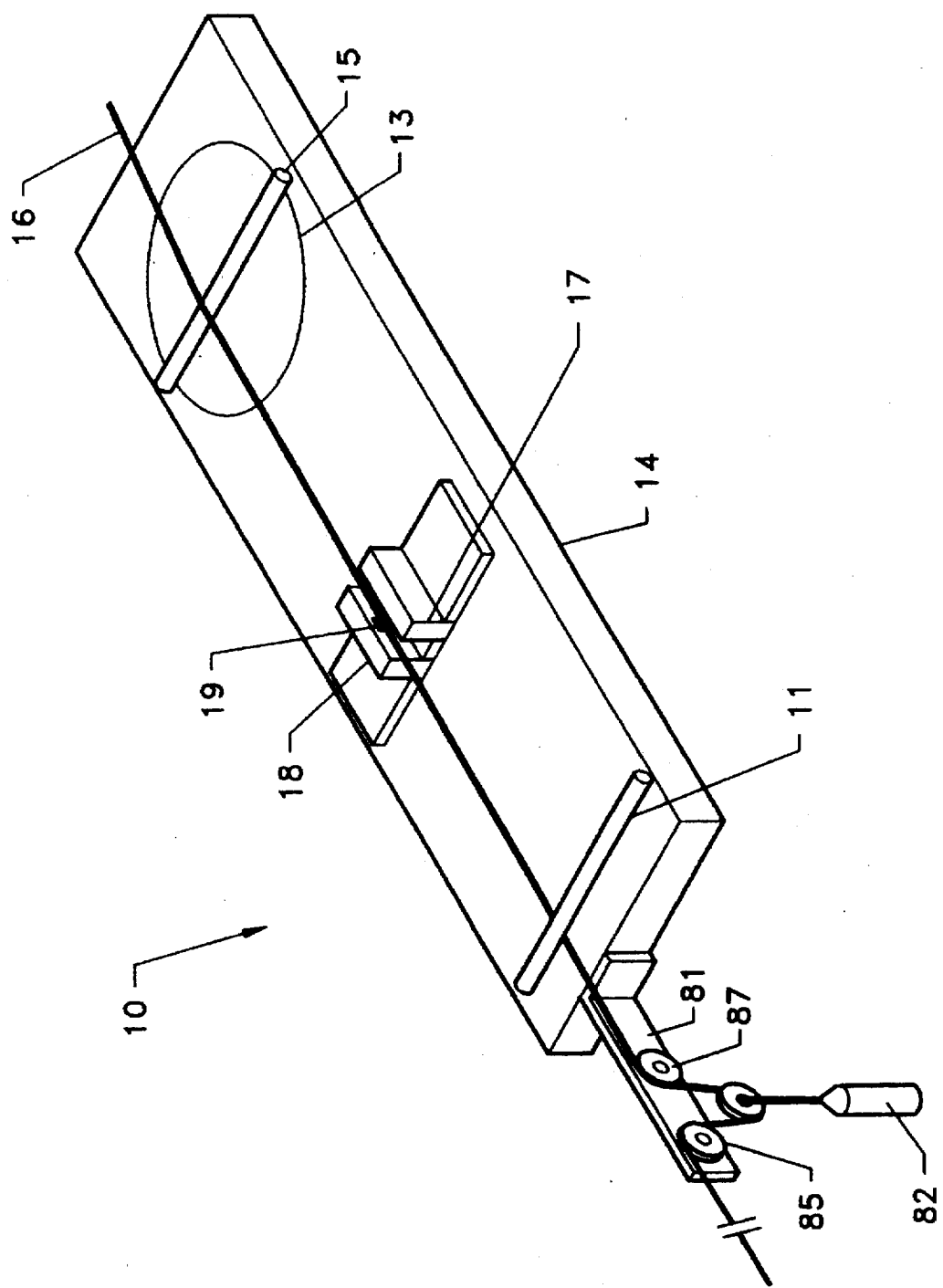
FIG. 1 is a perspective view of the mass measurement apparatus.

Referring now to FIG. 1, the apparatus for measuring filament density, designated generally by the reference numeral 10, is shown with its major components. The apparatus 10 has a fixed filament support 11 and a transducer 13 attached to a base 14. A moveable filament support 15 is attached to the transducer to provide a driver for inducing transverse vibrations into a filament 16. A light source 17 and photodetector 18 are mounted on base 14 and positioned with the suspended filament 16 passing between the light source and photodetector. An optical mask 19 is positioned between photodetector 18 and the moving filament 16 in order to provide a discrete signal to the photodetector during filament vibrations. A tensioning device 81 is affixed to base 14 to provide a uniform tension on filament 16. Weight 82 is suspended on filament 16 which is routed through pulleys 85 and 87. Although tension is normally on the filament during any manufacturing process, the tensioning device allows a uniform tension to be maintained. In some manufacturing processes where the tension in the filament is fairly uniform, the tensioning device may not be required.

The apparatus 10 provides a means of monitoring resin content or other coatings and impregnations in continuous fiber tows. The ability to provide continuous monitoring of both stationary and moving filaments ensures a uniform product when combining thermoplastic (powder coating) with continuous moving fibers. The determination of fiber or filament mass, and therefore the quantity of powder or resin applied, is accomplished by evaluating the vibrational characteristics of the fiber according to the following equation:

$$f = (1/2L)(T/m)^{(1/2)}$$

f=fundamental frequency (hz)
L=length (cm)
T=Tension (dyne)
m=mass density (g/cm)

Given a length of fiber under a known tension, the mass density can then be calculated based on the frequency response. More generally, if the string is moving axially in its lengthwise direction at a constant velocity v, then its resonant frequencies $f_n$ are given by $$f_n = (n/2L)(T/m)^{1/2}(1 - mv^2/T)$$

The Doppler shift given by the last term in parenthesis is significant when the velocity is large, as it may be in some manufacturing processes. Furthermore, if the vibrating element is thick or stiff, modifications to these equations can be made to reflect beamlike in addition to stringlike behavior.

Figure 2:
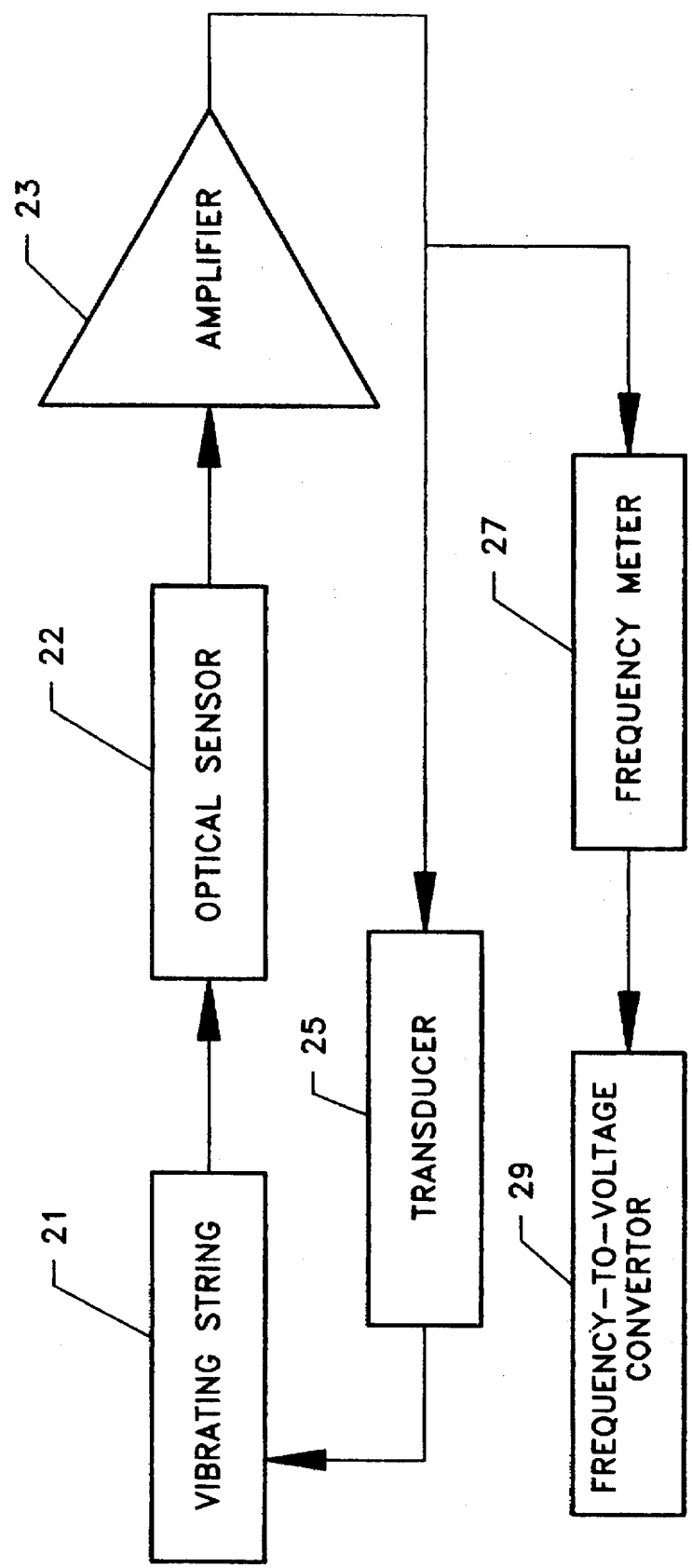
FIG. 2 is a block diagram of a self-tuning closed loop system.

Referring now to FIG. 2, the circuitry for collecting and processing data on the vibrating string of the preferred embodiment is shown by block diagram. The motion of the vibrating string 21 is detected by an optical sensor 22 or other means of detecting vibrational response. The signal from the optical sensor 22 is processed by amplifier 23. The amplified signal then drives transducer 25 at the natural resonance already occurring in the vibrating fiber. A part of the signal is directed to a display, in the preferred embodiment, a frequency meter 27 and to a frequency-to-voltage convertor 29 for control use.

Typically during the manufacturing of an impregnated or coated fiber, the high speed running of the fiber through the manufacturing devices will result in a natural vibration. Using the circuit of FIG. 2, the natural frequency will be amplified through the feedback circuit providing a self-tuned resonant response, thereby providing a resonantly vibrating string.

Figure 3:
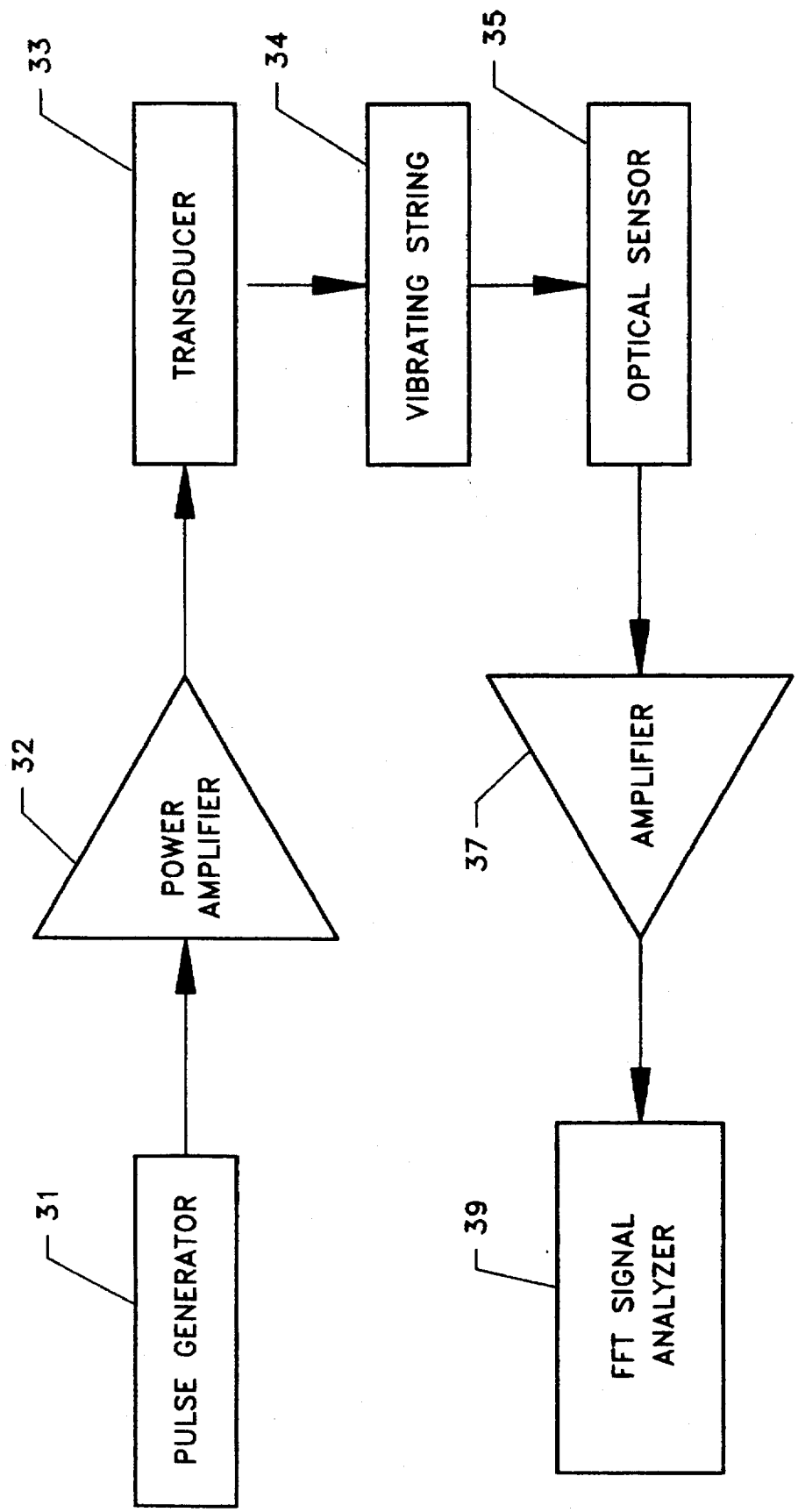
FIG. 3 is a block diagram of a pulsed excitation/free decay system.

It is also possible to produce a single-pulsed system wherein the fiber is transversely displaced by the single pulse thereby setting up a natural vibration followed by a gradual decay in amplitude. In this embodiment, shown in FIG. 3, the pulse generator 31 sends a driving pulse through power amplifier 32 to transducer 33 which in turn drives the vibrating string 34. As in the preferred embodiment, an optical sensor 35 detects the movement providing a signal to the amplifier 37. The output of amplifier 37 is then analyzed by the fast fourier transform analyzer 39 to determine the fundamental frequency.

Figure 4:
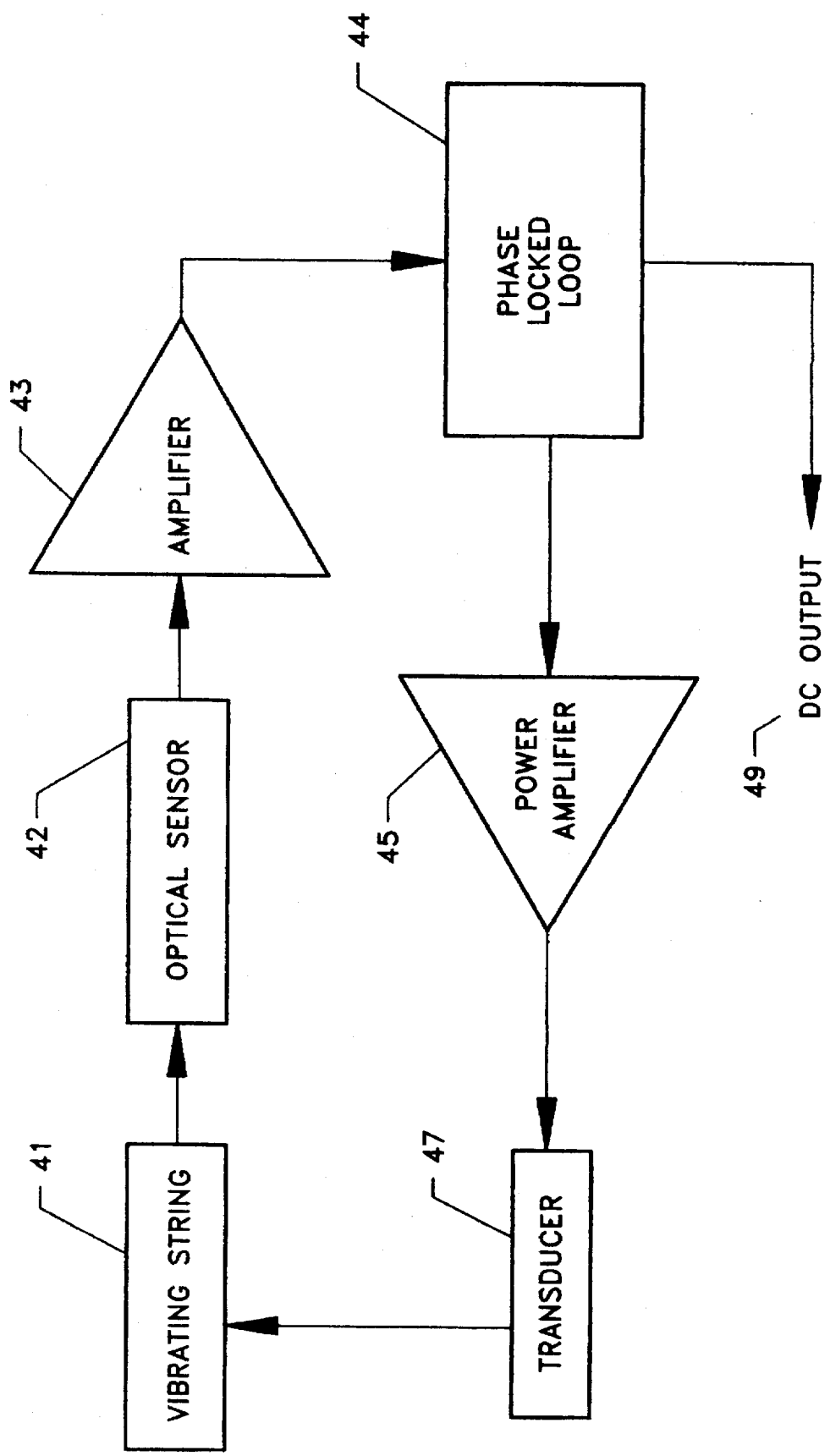
FIG. 4 is a block diagram of a phase-locked loop detector.

FIG. 4 depicts a further embodiment wherein the frequency of vibrating string 41 is detected by optical sensor 42 which feeds amplifier 43 to a phase locking component 44. This circuit provides feedback through power amplifier 45 to transducer 47 which in turn drives the vibrating string 41. DC output 49 provides a signal conditioned by the vibrational frequency.

Figure 5:
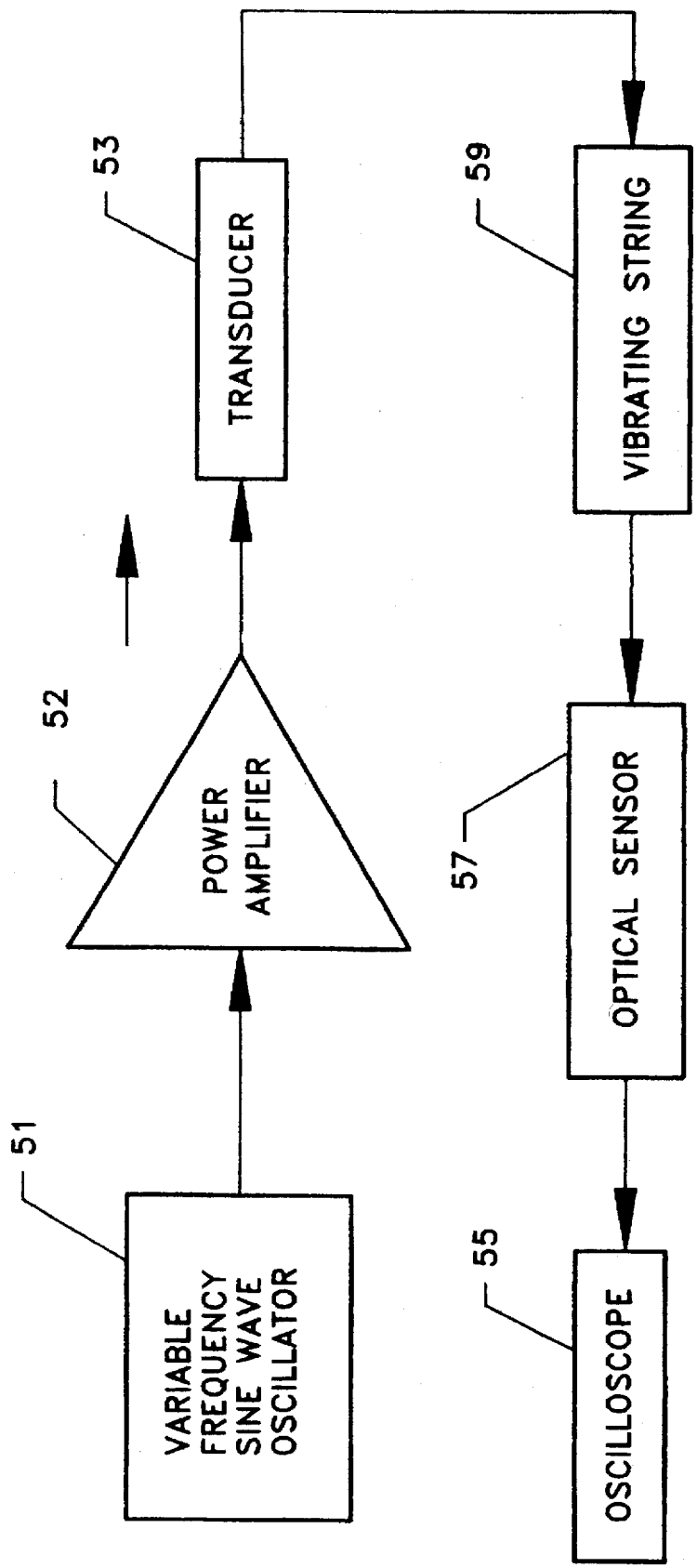
FIG. 5 is a block diagram of a variable input open loop detector.

Another variant of the invention, shown in FIG. 5, provides for a short duration excitation of the vibrating string over a specified frequency range. In this configuration, the variable frequency sine wave oscillator 51 provides a signal to a power amplifier 52 which drives the transducer 53. The signal provided causes the transducer 53 to initially vibrate at a frequency well below the resonant frequency of vibrating string 59. The vibrating frequency rapidly increases to a frequency well above the resonant frequency. During this frequency range sweep, the optical sensor 57 detects the vibrating string 59 response and provides a signal to oscilloscope 55 where the amplitude of the response identifies the resonant frequency.

Figure 6:
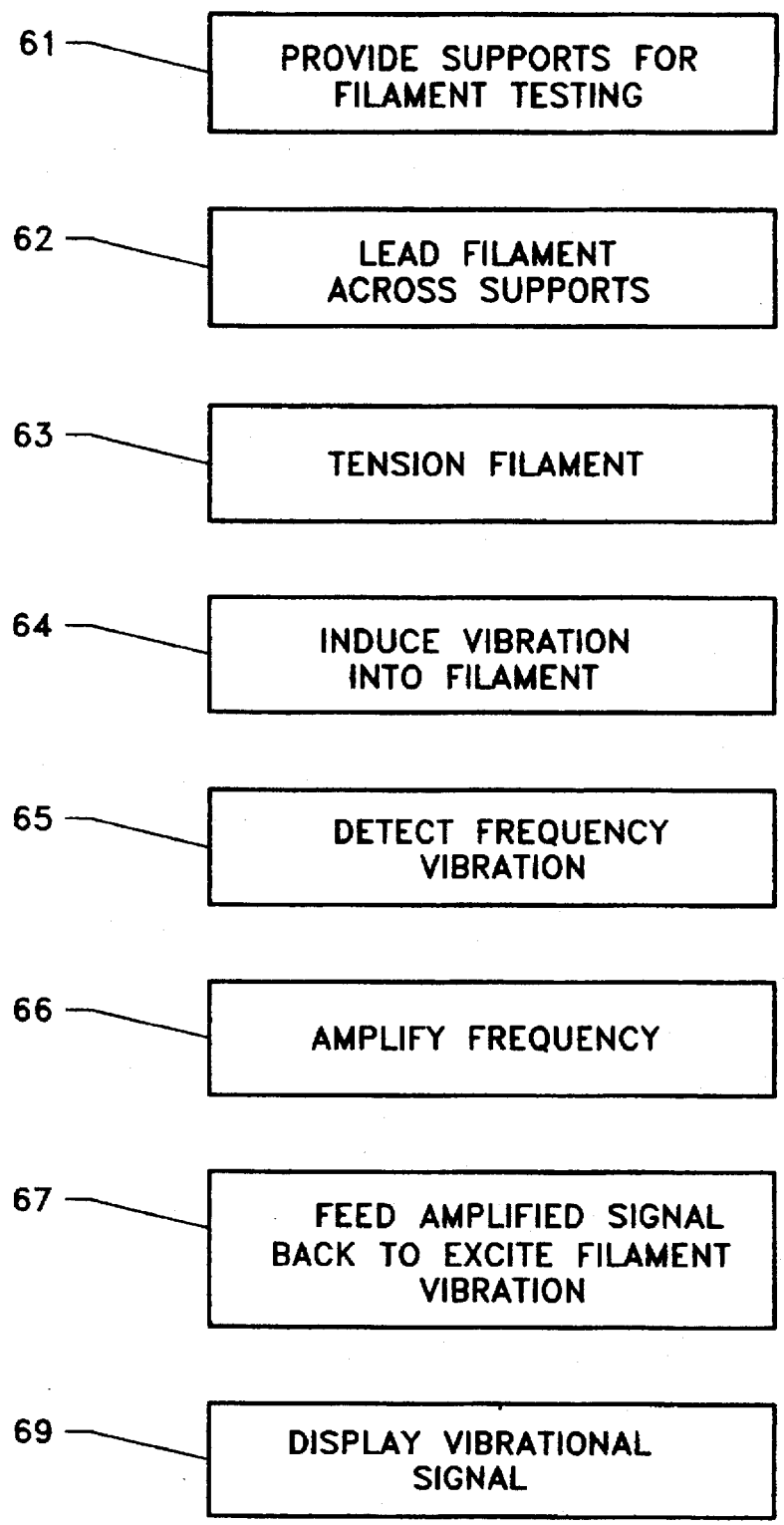
FIG. 6 is a flow chart delineating the steps in the process of the invention.

The method of the preferred embodiment is depicted in FIG. 6. The primary steps include providing two supports 61 for the filament or fiber; leading the filament across the supports 62; tensioning the filament 63; inducing vibrations into the filament 64; detecting the frequency of vibration 65; amplifying that frequency 66; feeding back the detected signal 67 to further excite the vibrational mode; and displaying the vibrational frequency 69. It is often necessary to perform every step specifically as some of the above-listed requirements may be provided by the underlying manufacturing process. For example, line tension may be sufficient without any additional tensioning from the invention. Likewise, there may be present, a natural vibration in a running fiber which can be amplified without the need to initially induce the vibration.

Figure 7:
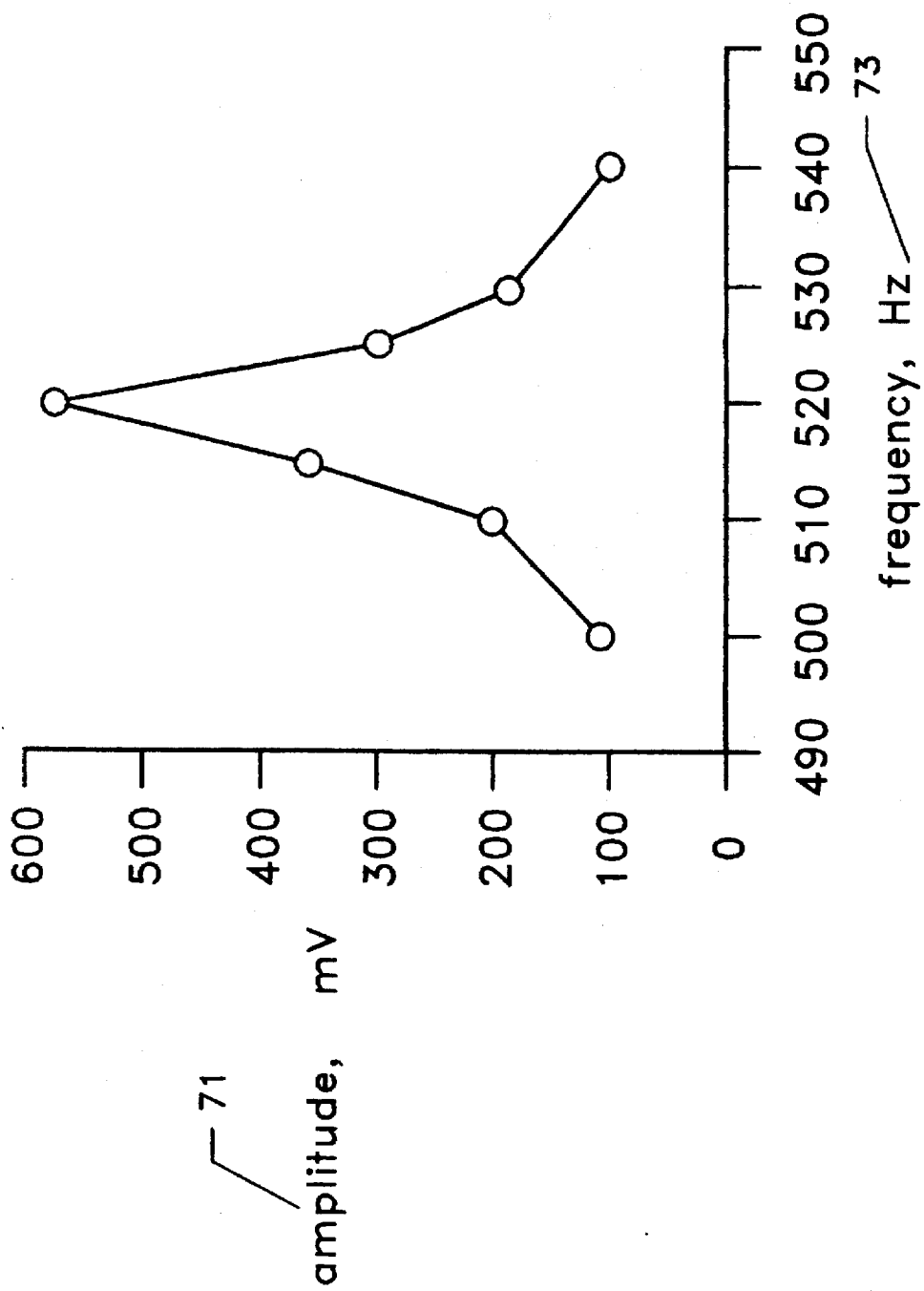
FIG. 7 is a graph of vibrational amplitude versus frequency produced by the variable input open-loop system.

Referring to FIG. 7, a plot of a typical response to a variable sine wave oscillator. The frequency 73 sweeps through the range of 500 to 540 Hz and the amplitude 71 has a maximum, indicating the resonant frequency, at 520 Hz.

The features and advantages of the invention are numerous. The mass density detector allows a variety of inputs to be used to excite vibration in the fiber to be tested. There is no requirement to stop the manufacturing process or remove the fiber from the manufacturing line. The fiber may be tested either running or in a stationary position.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed as new and desired to be secured by Letters Patent of the United States is:

1. An apparatus for determining mass density of a filament comprising:
   a base;
   a fixed filament support attached to said base;
   a transducer attached to said base;
   a moveable filament support attached to said transducer;
   a light source mounted on said base and aligned to illuminate a filament in contact with said filament supports;
   a photodetector mounted on said base and aligned to receive energy from said light source;
   an optical mask mounted on said base and located between said light source and said photodetector;
   a first amplifier mounted on said base and receiving the output of said photodetector; and
   a second amplifier mounted on said base and receiving a readout signal from said first amplifier and further providing an actuating electrical signal to said transducer.

2. An apparatus for determining mass density of a filament comprising;
   a base;
   means for inducing transverse vibration in a filament attached to said base:
   means for detecting filament vibrational response attached to said base; and
   means for displaying the vibrational response connected to said means for detecting, wherein said means for inducing transverse vibration further comprises a fixed filament support attached to said base.

3. An apparatus for determining mass density of a filament as in claim 2 wherein said means for inducing transverse vibration further comprises a transducer attached to said base.

4. An apparatus for determining mass density of a filament as in claim 3 wherein said means for inducing vibration further comprises a moveable filament support attached to said transducer.

5. An apparatus for determining mass density of a filament as in claim 3 wherein said means for inducing vibration further comprises a feedback circuit attached to said base and electrically connected to said transducer.

6. A method of determining filament density comprising the steps of:

resonantly vibrating a filament collecting data on the frequency of vibration of said filament: and processing said data to determine filament density, wherein said step of resonantly vibrating a filament further comprises setting a fixed length of filament for excitations.

7. A method of determining filament density as in claim 6 wherein said step of resonantly vibrating a filament further comprises tensioning said fixed length of filament.

8. A method of determining filament density as in claim 7 wherein said step of resonantly vibrating a filament further comprises inducing a transverse oscillation in the filament.

9. A method of determining filament density as in claim 6 wherein said step of collecting data further comprises illuminating said resonantly vibrating filament with a light source.

10. A method of determining filament density as in claim 9 wherein said step of collecting data further comprises receiving the interrupted illumination energy and converting such energy to electrical current.

11. A method of determining filament density as in claim 6 wherein said step of processing data further comprises amplifying the data signal, and analyzing said data using a fast-fourier transform analysis.

12. A method of determining filament density as in claim 11 wherein said step of processing data further comprises displaying the frequency domain resulting from said fast fourier transform analysis.

* * * * *